United States Patent [19] [11] 4,146,582
Maggioni [45] Mar. 27, 1979

[54] PROCESS FOR PREPARING AROMATIC ALDEHYDES AND KETONES

[75] Inventor: Paolo Maggioni, Cernusco Montevecchia, Italy

[73] Assignee: Brichima S.p.A., Milan, Italy

[21] Appl. No.: 764,422

[22] Filed: Jan. 31, 1977

[30] Foreign Application Priority Data

Jan. 30, 1976 [IT] Italy ............................... 19734 A/76

[51] Int. Cl.² ...................... C07C 45/02; C07C 45/16
[52] U.S. Cl. .................................. 260/592; 260/591; 260/599
[58] Field of Search ...................... 260/591, 592, 599

[56] References Cited

U.S. PATENT DOCUMENTS

| 1,939,212 | 12/1933 | Jaeger | 260/599 |
| 2,847,475 | 8/1958 | Voge et al. | 260/599 |
| 2,859,247 | 11/1958 | Radzitzky | 260/591 |
| 3,769,325 | 10/1973 | Fenton | 260/599 |
| 3,996,259 | 12/1976 | Lee et al. | 260/591 |

*Primary Examiner*—James O. Thomas, Jr.
*Assistant Examiner*—James H. Reamer
*Attorney, Agent, or Firm*—Joseph W. Molasky & Associates

[57] ABSTRACT

A method for preparing aromatic aldehydes and ketones in which the aldehydo or keto group is bonded directly to the aromatic ring; which comprises oxidizing an alkyl substituted aromatic compound or an aromatic compound which is substituted by an alpha-hydroxyalkyl moiety, via treatment with a persulfate and a metal catalyst. The metal catalysts include, for example, (1) iron salts and silver salts, or (2) a redox pair of salts such as an iron salt in combination with a copper salt or a silver salt in combination with a copper salt.

13 Claims, No Drawings

PROCESS FOR PREPARING AROMATIC ALDEHYDES AND KETONES

This invention relates to a new process for preparing aromatic aldehydes and ketones.

More precisely, this invention relates to a method for preparing aromatic aldehydes and ketones in which the aldehyde or ketone function is bonded directly to the aromatic nucleus, that is, to a nuclear carbon, by oxidizing an alkylbenzene or hydroxyalkylbenzene. The aldehyde and ketone products thus obtained are widely used in the chemical industry and they include such products as p-anisaldehyde, p-methoxy-acetophenone, veratraldehyde and the like.

The products of this process are important intermediates and include products to known utility in the secondary and fine chemical industry.

BACKGROUND

Many processes have been proposed for the preparation of these important products. Some of these use an alkylbenzene or an hydroxyalkylbenzene as the starting material for preparing specific products. However, in all instances the processes presently employed are either not of general use or are too complicated and costly for industrial purposes.

THE INVENTION

The process of this invention consists essentially of selectively oxidizing the carbon atom which is bonded to the aromatic nucleus. This oxidation results in the conversion of a nuclear bonded methyl or nuclear bonded hydroxymethyl group to an aldehyde moiety and, in the case of an alkyl or alpha-hydroxyalkyl of two or more carbon atoms, the oxidation results in the formation of the corresponding ketone.

More specifically, this invention provides a means for preparing aromatic aldehydes and ketones in which the aldehydo or keto group is bonded directly to the aromatic ring. This method consists essentially of subjecting an alkyl- or an hydroxyalkyl-aromatic compound of the formula: $Ar-CHXR^1$ wherein Ar is a mononuclear or binuclear aromatic radical, X is hydrogen or hydroxy and $R^1$ is hydrogen, lower alkyl or aryl to oxidation by treatment with a persulphate and a metal catalyst selected from among:

(1) an iron salt or a silver salt, or
(2) a redox pair of salts selected from the group consisting of an iron salt in combination with a copper salt or a silver salt in combination with a copper salt.

The preparation of the aldehyde and ketone products is best illustrated by reference to the following equations.

Equation A illustrates the preparation of an aldehyde by the oxidation of the corresponding arylmethane or an hydroxymethyl substituted aromatic compound:

(A) $Ar-CH_2X \xrightarrow{Oxidation} Ar-CHO$ wherein Ar is a mononuclear or binuclear aromatic radical such as phenyl, naphthyl or the like and X is hydrogen or hydroxy.

Equation B illustrates the preparation of an aryl ketone by the oxidation of an arylalkane in which the alkane moiety is straight or branched chain or, alternatively, the alkane moiety may be substituted at the alpha-carbon by an hydroxy or aryl radical:

(B) $Ar-CHXR \xrightarrow{Oxidation} Ar-COR$ wherein R is alkyl, preferably, lower alkyl such as methyl or ethyl and the like, or aryl such as phenyl or naphthyl and the like and Ar and X are as defined above.

The oxidation is effected with alkaline or ammonium persulphate in the presence of metal catalysts consisting of a redox pair of Fe/Cu or Ag/Cu salts.

Typical of the persulphate reagents which may be employed are, for example, the alkali metal derivatives such as sodium persulphate and the like, as well as the above-mentioned ammonium persulphate.

Preferably, the redox pair of metal catalysts consist essentially of an iron (e.g., ferrous) salt or a silver salt in an admixture with a cupric salt in solution.

As a practical matter, the iron and silver salts can be used in the practice of this invention without combining them with a copper salt; that is, the iron or silver salt alone will catalyze the persulphate-oxidation process to afford a good yield of product. However, it is only by associating the iron or silver salts with a copper salt that maximum yield is obtained; in excess of 90–95% yields in many instances.

The catalytic action of the copper salt seems to manifest itself essentially in inhibiting secondary processes, particularly dimerization, in favour of the primary oxidation process.

The most surprising aspect of the process of this invention is the extreme selectivity by which the formation of alcohols, carboxylic acids, dimerization products and other secondary products is minimized or completely eliminated.

The process is effected by gradually adding the persulphate, in powder form or in the form of a saturated aqueous solution, with accompanying fierce agitation, to the aromatic reactant dissolved in an inert organic solvent such as water or in a mixture of water and an inorganic solvent which is miscible with water.

The conditions which generally give best yields on the basis of the persulphate are those in which an aqueous solution of persulphate is gradually added, with agitation, to a mixture of the aromatic reactant and water containing small quantities of an organic solvent miscible with water. Particularly suitable organic solvents are methyl alcohol, ethyl alcohol, acetonitrile, acetone, acetic acid, dimethylformamide and acetamide.

The percentage of organic solvent which is employed in this process is on the order of 2–15% with respect to the water.

The following metal salts are particularly useful in the practice of this invention.

(a) all iron salts soluble in water, preferably, the salts of non-halogen or pseudo-halogen acids, such as sulphate, nitrate and acetate salts and the like;
(b) all silver salts soluble in water and, particularly the nitrate acetate and sulphate salts;
(c) all copper salts soluble in water and, preferably, sulphate, nitrate and acetate salts and the like.

The quantity of iron or silver salt used in this process is, preferably, 0.005 to 10 mole percent with respect to the aromatic reactant to be oxidized.

The copper salt is used in a Fe/Cu or Ag/Cu molar ratio of, preferably, between about 0.1 and 3.

The process is preferably carried out at a temperature between 10° and 100° C.

Theoretically, two moles of persulphate are required to oxidize one mole of alkybenzene, and one mole of persulphate is required to oxidize one mole of a primary or secondary alpha-aryl alcohol. In practice, 1 to 3 moles of persulphate are used per mole of aromatic compound. The use of a deficiency of excess of persulphate is linked essentially to two factors:

(a) the cost of the two main raw materials, i.e., the persulphate and aromatic compound;
(b) the cost of recovering and recycling the aromatic compound in the case of a partial conversion.

Generally, the yield of product decreases slightly with an increase in the ratio of persulphate to the aromatic compound. Therefore, when the excess of starting material is easy to separate from the oxidation product (which, in the majority of cases, can be accomplished by distillation) it is preferable to work with a deficiency of persulphate so as to achieve a partial conversion of the alkyl derivative or the primary or secondary α-aryl alcohol, preferably between 30 and 50%.

However, when the starting compound is not easily separable from the oxidation product, or when only one of the various substrates present in a mixture is to be selectively oxidized, it is preferable to work with a stoichiometric quantity or slight excess of persulphate so as to convert the largest possible part of the desired substrate.

As stated, the present process is characterized by high intramolecular and intermolecular selectivity, which leads to considerable practical advantages. Therefore, it is possible to selectively oxidize a methyl group to an aldehydo moiety with a high conversion and without obtaining an appreciable amount of carboxylic acid (this is a result of considerable practical interest considering the ease of oxidation of aldehydes).

It is also possible to selectively oxidize a single alkyl group in a polyalkylbenzene while avoiding the formation of complex mixtures of mono- and polyoxidation products.

Another very important aspect of the present process is the fact that its high intermolecular selectivity may be utilized for oxidizing mixtures of isomers which are difficult to separate. This is the case for example of mixtures of para- and meta-cresol which are very difficult to separate both as methyl ethers, because they have very similar properties and very close boiling points.

Consequently, the cost of mixtures of industrial origin is considerably less than the cost of the pure isomers, and their use is extremely convenient.

In using the present process to oxidize a mixture of methyl ethers of meta- and para-cresol containing 30 to 70% of the para-isomer, there is a surprising selective oxidation of the para-isomer. This results in a mixture of p-anisaldehyde and the methyl ether of meta-cresol and the former (aldehyde) may be easily recovered from this mixture because of the very different boiling points of the two products.

This invention will now be described by reference to specific examples. However, it is to be understood that these examples are illustrative only and are not limitative. Therefore, any substitution of equivalent materials or modification in the reaction conditions is considered as being within the scope of this invention and not a departure therefrom.

The Embodiments

The process of this invention will be evident from the following Examples.

EXAMPLE 1 p-Anisaldehyde

Ferrous-Copper Catalyst: p-Cresol-methylether (502.5 g.), water (1750 ml.), ferrous sulphate heptahydrate (4.56 g.), cupric acetate (8.87 g.) and methanol (400 ml.) are placed in a 10 liter reactor.

An aqueous-methanol solution (2005 g.) containing 24% of sodium persulphate is added by dripping same into the mixture thus prepared, with agitation, at 70° C. and in a nitrogen atmosphere.

The completion of the reaction is checked by titration about two hours after the addition of the sodium persulphate is completed.

The organic phase is separated from the aqueous phase by extraction with ethyl ether.

By rectifying the collected organic phases 34.400 g. of p-cresol-methylether are obtained and recycled, and 4.54.6 g. of p-anisaldehyde (yield 87.5%) is obtained.

A similar test was carried out using a catalyst based only on a ferrous salt catalyst.

Ferrous Catalyst: p-Cresol-methylether (50.25 g.), water (175 ml.), ferrous sulphate heptahydrate (0.910 g.) and methanol (40 ml.) are placed in a two liter reactor.

The temperature of the mixture is raised to 70° C. and an aqueous-methanol solution of sodium persulphate (202 g.) are dripped into same with agitation. The oxidant is expended within 2 hours 30 minutes after dripping same into the said mixture.

The organic phase is separated and the aqueous phase is extracted with ethyl ether.

p-Cresol-methylether (8.1 g.) is collected and recycled, and 32.8 g. of p-anisaldehyde (yield 70%) are obtained from the collected organic phases.

On the basis of this experiment, it is apparent that the use of a ferrous based catalyst alone does not afford the same high yields which result from the use of a combination of ferrous and copper based catalyst.

EXAMPLE 2 p-Anisaldehyde

Silver-Copper Catalyst: p-Cresol-methylether (502.7 g.), a 0.1 N solution of silver nitrate (205 ml.), cupric acetate (3.63 g.), water (1745 ml.) and methanol (410 ml.) are placed in a 10 liter reactor.

An aqueous-methanol solution of sodium persulphate (1870 g.) is slowly dripped into the said mixture. The oxidant disappears one hour after addition has finished.

By extracting and distilling as described in Example 1, 25 g. of p-cresol-methylether and 478.57 g. of p-anisaldehyde (yield 90%) are obtained.

Silver Catalyst: By repeating the above procedure, but without using cupric acetate, the p-cresolmethylether disappears completely to afford p-anisaldehyde in a 40% yield. Also obtained are polymer by-products which concentrate as a distillation residue.

From this experiment it is apparent that the use of a silver-copper catalyst is superior to the use of a silver catalyst alone.

EXAMPLE 3 p-Anisaldehyde

Ferrous-Copper Catalyst: p-Cresol-methylether (50.2 g.), water (100 ml.), ferrous sulphate heptahydrate (0.4588 g.), cupric acetate (0.8869 g.) and acetonitrile (80 ml.) are placed in a two liter reactor.

Sodium persulphate (194 g.) in aqueous solution are dripped into the mixture at 70° C. with agitation and in a nitrogen atmosphere.

Upon completion of the reaction, p-anisaldehyde is isolated in the manner described in the previous Examples.

EXAMPLE 4 p-Anisaldhyde

Ferrous-Copper Catalyst: A mixture (493.2 g.) of m-cresol-methylether and p-cresol-methylether (75% p-isomer), water (1700 ml.), ferrous sulphate heptahydrate (4.5 g.), cupric acetate (4.5 g.) and methyl alcohol (400 ml.) are placed in a 10 liter reactor. An aqueous-methanol solution of sodium persulphate (1650 g.) is added slowly to the mixture under agitation at 70° C. and in a nitrogen atmosphere.

The organic phase is separated at the end of the reaction and rectified. p-Anisaldehyde (348.5 g., yield 84.5%) and meta-cresol-methylether (110.60 g.) with an isomer purity of not less than 98% as determined by comparison with pure isomers using NMR, are obtained.

EXAMPLE 5

Benzaldehyde

Ferrous-Copper Catalyst: Toluene (7.6 g.), water (35 ml.), ferrous sulphate (0.110 g.) heptahydrate, cupric acetate (0.072 g.) and methanol (8 ml.) are placed in a 250 ml. reactor.

Sodium persulphate (47.05 g.) in an aqueous-methanol solution of sodium persulphate is added slowly to the mixture which is maintained at 70° C., in an atmosphere of nitrogen and under agitation.

The organic phase is separated after two hours and the aqueous phase is extracted with ethyl ether.

The combined organic phases are distilled to afford 8.29 g. (95% yield) of very pure benzaldehyde (compared against a pure sample).

EXAMPLE 6 p-Tolualdehyde

Ferrous-Copper Catalyst: Example 5 is repeated but using p-xylene instead of toluene. The para-tolualdehyde (75% yield) is isolated from the reaction mixture and identified by mass spectrophotometry.

EXAMPLE 7 p-Methoxyacetophenone

Ferrous-Copper Catalyst: p-Ethylanisole (10 g.), ferrous sulphate heptahydrate (0.0805 g.), copper acetate (0.1538 g.), demineralized water (35 ml.) and methanol (8 ml.) are placed in a 250 ml. reactor.

The reaction temperature is raised to 80° C. and a flow of nitrogen is fed to the reactor. Agitation of the reaction mixture is fierce.

An aqueous-methanol solution of sodium persulphate (42 g. in 133 ml. of $H_2O$ and 8 cc of $CH_3OH$) are dripped in. The reaction is completed after two hours.

The p-methoxyacetophenone thus produced is separated from the aqueous phase and, after distillation, p-ethylanisole (0.60 g.) and p-methoxyactophenone (8.28 g.) are obtained and identified by comparison with a pure sample. The yield of p-methoxyacetophenone is 80%.

EXAMPLE 8

Veratraldehyde

Ferrous-Copper Catalyst: 3,4 Dimethoxytoluene (10 g.), ferrous sulphate heptahydrate (0.0728 g.), demineralized water (50 ml.), copper acetate (0.1426 g.) and methanol (8 ml.) are placed in a 250 cc reactor.

The reaction temperature is raised to 60° C. while feeding a nitrogen flow to the reactor.

An aqueous-methanol solution of sodium persulphate (37.52 g. in 118.8 ml. of $H_2O$ and 8 cc of $CH_3OH$) are dripped in. The reaction is completed within three hours.

The veratraldehyde produced is separated from the aqueous phase and, after distillation, 0.99 g. of 3,4-dimethoxytoluene and 5.83 g. of veratraldehyde (60% yield) identified by comparison with an authentic sample, are obtained.

EXAMPLE 9 p-Anisaldehyde

Ferrous-Copper Catalyst: Anisic alcohol (50 g.), ferrous sulphate heptahydrate (0.3892 g.) copper acetate (0.7783 g.), demineralized water (100 ml.) and methanol (40 ml.) are placed in a reactor.

The temperature of the reaction mixture is raised to 80° C. and a flow of nitrogen is fed to the reactor under fierce agitation while commencing to drip feed a solution of sodium persulphate (103.4 g of $Na_2S_2O_8$ in 335 ml. of $H_2O$). The reaction is complete within two hours.

The reaction products are extracted with ethyl ether and, after evaporation of the solvent, 0.8 g. of anisic alcohol and 43.86 g of p-anisaldehyde are obtained by distillation at 100 mm Hg.

The yield of p-anisaldehyde with respect to the reacted anisic alcohol is 90.50%.

What is claimed is:

1. A method for preparing aromatic aldehydes or ketones in which the aldehyde or keto moiety is bonded directly to the aromatic ring; which comprises subjecting a compound of the formula:

Ar—CHXR[1] 

wherein Ar is a mononuclear or binuclear aromatic radical, X is hydrogen or hydroxy and $R^1$ is hydrogen, lower alkyl or aryl; to oxidation by treatment with a catalytic amount of a water soluble metal salt selected from:

(1) a ferrous salt or silver salt, or
(2) a redox pair of salts selected from the group consisting of a ferrous salt in combination with a cupric salt, or a silver salt in combination with a cupric salt followed by the slow addition of 1-3 moles of alkali metal persulphate or ammonium persulphate per mole of aromatic aldehyde or ketone.

2. The method according to claim 1 for preparing an aldehyde of the formula:

Ar—CHO 

wherein Ar is a mononuclear or binuclear aromatic radical; which comprises treating a compound of the formula:

Ar—CH$_2$X 

wherein X is hydrogen or hydroxy and Ar is as defined above, with a catalytic amount of a water soluble metal salt selected from:
(1) a ferrous salt or a silver salt, or
(2) a redox pair of salts selected from the group consisting of a ferrous salt in combination with a cupric salt or a silver salt in combination with a cupric salt followed by the slow addition of 1–3 moles of alkali metal persulphate or ammonium persulphate per mole of aromatic aldehyde or ketone.

3. The method according to claim 1 for preparing a ketone of the formula:

Ar—COR wherein Ar is a mononuclear or binuclear aromatic radical and R is alkyl, phenyl or naphthyl; which comprises treating a compound of the formula:

Ar—CHXR wherein X is hydrogen or hydroxy and Ar and R are as defined above, with a catalytic amount of a water soluble metal salt selected from:
(1) a ferrous salt or a silver salt, or
(2) a redox pair of salts selected from the group consisting of a ferrous salt in combination with a cupric salt, or a silver salt in combination with a cupric salt
followed by the slow addition of 1–3 moles of alkali metal persulphate or ammonium persulphate per mole of aromatic aldehyde or ketone.

4. The method of claim 2 wherein the oxidizing agent is alkali metal persulphate or ammonium persulphate and a redox pair of salts selected from the group consisting of a ferrous salt in combination with a cupric salt or a silver salt in combination with a cupric salt.

5. The method of claim 3 wherein the oxidizing agent is alkali metal persulphate or ammonium persulphate and a redox pair of salts selected from the group consisting of a ferrous salt in combination with a cupric salt or a silver salt in combination with a cupric salt.

6. The method of claim 1 wherein the persulphate is used in powder form or in a saturated aqueous solution.

7. The method of claim 1 wherein the iron salts which are used alone or in combination with the copper salts are water soluble and are selected from the group consisting of sulphate, nitrate and acetate salts.

8. The method of claim 1 wherein the silver salts which are used in combination with the copper salts are water soluble and are selected from the group consisting of nitrate, acetate and sulphate salts.

9. The method of claim 1 wherein the copper salts which are used in combination with the iron salts and silver salts are water soluble and are selected from the group comprising sulphate, nitrate and acetate salts.

10. The method of claim 1 wherein the iron or silver salts are used in molar quantities of between about 0.005 and 10% of the aromatic compound which is to be oxidized and the copper salt is employed in an iron to copper or silver to copper molar ratio of between about 0.1 and 3.

11. The method of claim 1 wherein the reaction is conducted in the presence of an inert medium selected from the group consisting of an organic solvent or a mixture of water and an organic solvent.

12. The method of claim 11 wherein the organic solvent is methyl alcohol, ethyl alcohol, acetonitrile, acetone, acetic acid, dimethyl-formamide or acetamide.

13. The method of claim 1 wherein the reaction is conducted at a temperature of from about 10° to 100° C.

* * * * *